United States Patent [19]

Naiini et al.

[11] Patent Number: 5,834,581
[45] Date of Patent: *Nov. 10, 1998

[54] PROCESS FOR MAKING POLYIMIDE-POLYAMIC ESTER COPOLYMERS

[75] Inventors: Ahmad Naiini, Warwick; Steve L. C. Hsu, East Providence; William D. Weber, Cranston, all of R.I.; Andrew J. Blakeney, Seekonk, Mass.

[73] Assignee: Olin Microelectronic Chemicals, Inc., Norwalk, Conn.

[*] Notice: The term of this patent shall not extend beyond the expiration date of Pat. No. 5,789,524.

[21] Appl. No.: 839,692

[22] Filed: Apr. 15, 1997

[51] Int. Cl.⁶ .......................... C08G 73/12; C08G 69/26
[52] U.S. Cl. .................. 528/170; 528/125; 528/128; 528/142; 528/143; 528/183; 528/188; 528/220; 528/229; 528/272; 528/322; 528/332; 528/350; 528/353; 524/600; 524/606
[58] Field of Search ............................ 528/310, 125, 528/179, 128, 172, 173, 183, 188, 220, 229, 272, 322, 332, 350, 353; 524/600, 606

[56] References Cited

U.S. PATENT DOCUMENTS

| | | | |
|---|---|---|---|
| 3,179,630 | 4/1965 | Endrey | 524/600 |
| 3,179,632 | 4/1965 | Hendrix | 524/600 |
| 3,271,366 | 9/1966 | Kreuz | 524/600 |
| 3,282,898 | 11/1966 | Angelo | 528/310 |
| 3,541,057 | 11/1970 | Kreuz | 524/600 |
| 5,302,489 | 4/1994 | Shu | 430/191 |
| 5,399,655 | 3/1995 | Simmons, III | 528/128 |
| 5,587,275 | 12/1996 | Kato | 430/283.1 |

FOREIGN PATENT DOCUMENTS 0 421 195 A2   4/1991   European Pat. Off. .

OTHER PUBLICATIONS

Mitsuru Ueda et a., *Macromolecules 1988*, 21, 19–24, The month of the date of publication is not available.

E. Chin et al., *Advances in Polyimide Science and Technology–Proceedings of the Fourth International Conferecne on Polyimdes*, Edited by C. Feger et al., 1993, pp. 201–202, Technonic Publishing Co., Ltd., Lancaster, PA.

Hayase et al., *Journal of Applied Polymer Science*, vol. 51, pp. 1971–1978 (1994) The month of the date of publication is not available.

M. Ueda et al., *Makromol. Chem.*, 194, pp. 511–521 (1993) The month of the date of publication is not available.

Primary Examiner—P. Hampton-Hightower
Attorney, Agent, or Firm—Ohlandt, Greeley Ruggiero, & Perle

[57] ABSTRACT

A process for making polyimide-polyamic ester copolymer composition comprising reacting at least one diamine, a pyromellitic diacid diester compound; at least one other tetracarboxylic diacid diester compound and a selected phosphoramide in the presence of a base catalyst to form a polyimide-polyamic acid ester copolymer.

2 Claims, No Drawings

PROCESS FOR MAKING POLYIMIDE-POLYAMIC ESTER COPOLYMERS

BACKGROUND OF THE INVENTION

1. Field of the Invention

This invention relates to a process for making polyimide-polyamic acid ester copolymers by reacting a diamine, at least two different tetracarboxylic diacid diesters with a specific imidization reagent to form a polyimide-polyamic acid ester copolymers. These polyimide polyamic acid ester copolymers may be used as a precursor for polyimide compounds that may be useful as organic dielectric insulating films for use in electronic semiconductor devices and multilayer electronic structures; as protective coatings on or in electronic semiconductor devices and packages; as oriented films for use in the fabrication of liquid crystal display elements; as matrix resins in structural composites; and as membranes for use in separation processes. These copolymers may also be employed as precursors for photosensitive polyimide formulations.

2. Brief Description of the Art

Aromatic polyimides are usually synthesized by a two-step method. In the first step, polyamic acid is formed by the reaction of at least one diamine with at least one dianhydride. In the second step, dehydrative cyclization ("imidization") of the polyamic acid creates the polyimide. The imidization reaction can be carried out by heating at elevated temperatures, usually 150–3000° C., or by treatment with chemical imidization agents at ambient temperature. The most commonly used dehydrating agents are the combination of an acid anhydride with a base catalyst. The acid anhydrides used in the past include acetic anhydride, propionic anhydride, n-butyric anhydride, benzoic anhydride and the like. The base catalysts used in the past included pyridine, trialkylamines, methylpyridine, lutidine, n-methylmorpholine, and the like. Alternatively, polyamic acid esters have been used in the past instead of polyamic acids as precursors for polyimides. However, because of their higher cost, polyamic acid esters have not been favored.

Separately, the synthesis of diphenyl(2,3-dihydro-2-thioxo-3-benzoxazoyl)phosphonate (DDTBP) and its use as an activating agent for polyamic acid esters was first reported by Mitsuru Ueda et al. See (*Macromolecules* 1988, 21, 19–24). Its structure is shown as following formula (1):

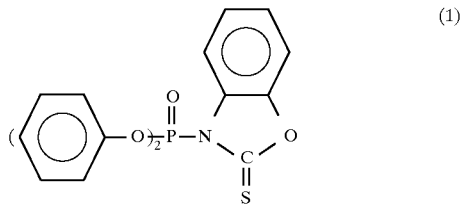

Recently, E. Chin et al.(see *Advances in Polyimide Science and Technology—Proceedings of the Fourth International Conference on Polyimides*, Edited by C. Feger et al., 1993, pages 201–212, Technonic Publishing Co., Ltd., Lancaster, Pa.) teach the use of DDTBP as a coupling reagent to prepare polyamic acid esters by the direct polycondensation from tetracarboxylic diacid diester monomers.

Also Hayase et al. (see *Journal of Applied Polymer Science*, Vol. 51, pages 1971–1978 (1994)) teach the reaction of a tetracarboxylic diacid diester with a diamine to form a polyamic acid. diester.

And, M. Ueda et al. (see *Makromol. Chem.*, 194, 511–521 (1993) teach the direct polycondensation of di-tert-butyl esters of tetracarboxylic acids with diamines to make polyamic acid tert-butyl-esters, using DDTBP as the activating agent.

None of these references reported that DDTBP may be used as a selective chemical imidization agent for making polyimides.

The present invention involves a novel process for the synthesis of desirable polyimide-polyamic acid ester copolymers from diamines and a mixture of diesters compounds by selective chemical imidization using a particular class of phosphoramides including DDTBP as a selective chemical imidization reagent.

SUMMARY OF THE PRESENT INVENTION

Accordingly, the present invention relates to a process for making polyimide-polyamic acid ester copolymers comprising reacting at least one diamine, at least one diester of pyromellitic dianhydride compound, at least one other tetracarboxylic diacid diester compound; and a phosphoramide in the presence of a base catalyst to form polyimide-polyamic ester copolymer, wherein said phosphoramide is a compound of formula (2):

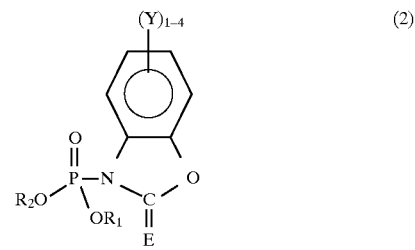

wherein

E is either oxygen or sulfur; $R_1$ and $R_2$ are individually selected from alkyl group having 1–4 carbon atoms; aryl group; substituted aryl group having 1–3 substituents wherein said substituents are individually selected from halogen group, nitro group, alkyl group having 1–4 carbon atoms; and each Y is individually selected from hydrogen, halogen group, nitro group, alkyl group having 1–4 carbon atoms and alkoxy group having 1–4 carbon atoms.

DETAILED DESCRIPTION OF THE PREFERRED EMBODIMENTS

This invention relates to the process of preparing desired polyimide-polyamic ester copolymers from diamines and a mixture of diester compounds by selective chemical imidization. In this process the chemoselective property of certain phosphoramides such as DDTBP has been employed to synthesize the desired polyimide-polyamic ester copolymer.

This copolymer should be synthesized from at least one diamine and at least two tetracarboxylic diacid diesters which one of them should be a diester of pryomellitic dianhydride (PMDA) compound. This reaction is illustrated by the following reaction equation:

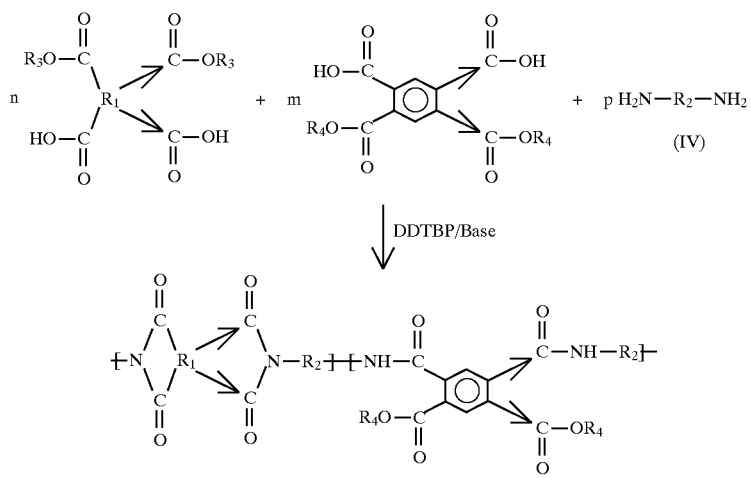

wherein $R_1$ is a substituted or unsubstituted tetravalent, $R_2$ is a substituted or unsubstituted divalent radical, $R_3$ and $R_4$ are substituted or unsubstituted monovalent radicals; $R_3$ and $R_4$ can be the same or they can be different and $1.10p \geq m+n \geq 0.90p$.

1) Preferred Phosphoramides

The preferred phosphoramide is diphenyl (2,3-dehydro-2-thioxo-3-benzoxazoyl) phosphonate (DDTBP) or where E is sulfur; $R_1$ and $R_2$ are both phenyl groups and all Y groups are hydrogen. The preferred method for making DDTBP is that described by Ueda et al. (*Macromolecules* 1988, 21, 19–24) except that toluene is used instead of benzene.

2) Preferred Pyromellitic Dianhydride Diacid Diesters Compounds

The diesters of pyromellitic dianhydride (PMDA) may be prepared by the reaction of pyromellitic dianhydride with two moles of an alcohol or phenol. This reaction produces different isomers of PMDA diesters as indicated in the following reaction equation:

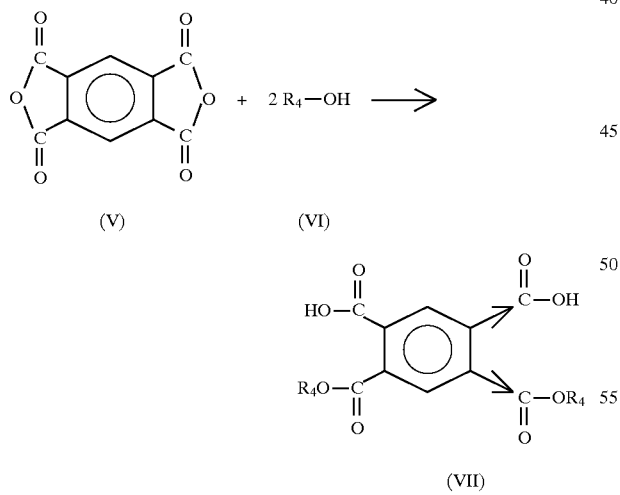

The alcohol or phenol compounds (VI) used in this process could be, but are not restricted to, the following: methyl alcohol, ethyl alcohol, isopropyl alcohol, n-butyl alcohol, t-butyl alcohol, 2-hydroxybenzyl alcohol, 3-hydroxybenzyl alcohol, 4-hydroxybenzyl alcohol, 2-hydroxyethylmethacrylate, 2-hydroxyethylacrylate, tetrahydropyranol, tertbutoxyacetyl, and a mixed alkoxy acetal ester.

The term "pyromellitic dianhydride compound" as used in the present specification and claims includes pyromellitic dianhydride (PMDA) as well as those similar PMDA. compounds wherein the aromatic ring is substituted in either the 3- or 6-position, or both positions. An example of such a similar PMDA compound covered hereunder is 3,6-diphenylpyromellitic dianhydride.

3) Preferred Other Tetracarboxylic Diacid Diesters

The other tetracarboxylic diacid diesters can be prepared by reaction of tetracarboxylic dianhydride by two moles of an alcohol or phenol derivatives according to the reaction below. This reaction produces different isomers of tetracarboxylic diacid diesters. The isomerization is represented by arrows in compounds (III) and (VI).

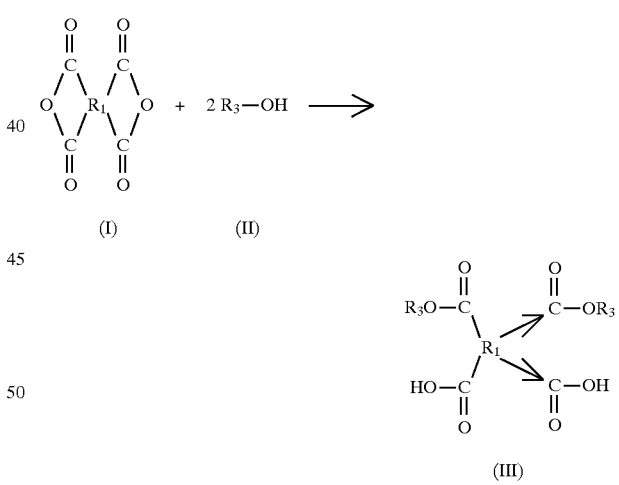

The tetracarboxylic dianhydride (I) could be but is not restricted as following: 3,3',4,4'-benzophenonetetracarboxylic dianhydride, 3,3',4,4'-biphenyltetracarboxylic dianhydride, 3,3',4,4'-diphenylsulfonetetracarboxylic dianhydride, 4,4'-perfluoroisopropylidinediphthalic dianhydride, 4,4'-oxydiphthalic anhydride, bis(3,4-dicarboxyl) tetramethyldisiloxane dianhydride, bis(3,4-dicarboxylphenyl) dimethylsilane dianhydride, butane tetracarboxylic dianhydride, and 1,4,5,8-naphthalenetetracarboxylic dianhydride. These tetracarboxylic dianhydrides can be used singly or in combination.

The alcohol or phenol compounds used in this reaction may be the same as used in the making of the PMDA diester as listed above. The same reaction conditions noted above for making the PMDA diester may be used for making these other tetracarboxylic diacid diesters.

4) Preferred Diamines

The preferred diamine (IV) used in this process could be but is not restricted as following: m-phenylenediamine, p-phenylenediamine, 2,2'-bis(trifluoromethyl)-4,4'-diamino-1,1'-biphenyl, 3,4'-diaminodiphenyl ether, 4,4'-diaminodiphenyl ether, 3,3'-diaminodiphenyl ether, 2,4'-tolylenediamine, 3,3'-diaminodiphenyl sulfone, 3,4'-diaminodiphenyl sulfone, 4,4'-diaminodiphenyl sulfone, 3,3'-diaminodiphenylmethane, 4,4'-diaminodiphenylmethane, 3,4'-diaminodiphenylmethane, 4,4'-diaminodiphenyl ketone, 3,3'-diaminodiphenyl ketone, 3,4'-diaminodiphenyl ketone, 1,3-bis(4-aminophenoxy) benzene, 1,3-bis(3-amino-phenoxy) benzene, 1,4-bis(γ-aminopropyl)tetramethyldisiloxane, and 4,4'-diaminodiphenyl sulfide and 1,3,3-trimethylphenylindane diamine. These diamines can be used singly or in combination.

5) Preferred Base Catalyst

The base catalyst used in this process could be but is not restricted to a base such as pyridine, trialkylamine, methylpyridine, lutidine, n-methylmorpholine, and the like. It is preferred to use tertiary amines and the most preferred base is triethylamine.

6) Preferred Reaction Conditions for Polyimide-Polyamic Ester Copolymer Formation The preferred polymerization/imidization procedure is adding a diamine or a mixture of diamines to the mixture of tetracarboxylic diacid diesters in solution followed by addition of a base such as tertiary amine to this mixture. The phosphoramide such as DDTBP should then be added slowly to the mixture. The reaction temperature must be in the range of 35° C. to 60° C. The preferred reaction time is 8 hours to 24 hours. The stoichiometric amount of diamine should be substantially equal to the total moles of PMDA and the other tetracarboxylic diacid diester. The stoichiometric amount of phosphoramide such as DDTBP, as well as the base should be at least twice as much as total moles of PMDA and others tetracarboxylic diacid diesters or the moles of diamines. The preferred stoichiometric amount of these two reagents is 2.2–4.4 times of tetracarboxylic diacid diesters or diamines. The formation of polymer is confirmed by measuring the inherent viscosity of the product and the imidization is confirmed by the appearance of a strong absorption at 1778 cm$^{-1}$ (characteristic of imides) in FTIR spectrum. The absence or substantial reduction of esters peaks of tetracarboxylic diacid diesters (other than diesters of pyromellitic dianhydrides and its derivatives) and presence of ester peaks of diesters of pyromellitic dianhydrides and its derivatives in the NMR spectrum is indicative of selective imidization in this process.

7) Conversion of Polyimide-polyamic Acid Ester Copolymer to Polyimide-polyamic Acid Copolymer The polyimide-polyamic acid ester copolymers may be converted to polyimide-polyamic acid copolymer by reaction of the polyimide-polyamic acid ester with a suitable chemical reagent chosen for this purpose. The reagent to be chosen will depend on the structure and reactivity of the ester group constituted in the polyimide-polyamic acid ester copolymer. The preferred reagents could be, but are not restricted to: alkali metal hydroxides, alkaline earth metal hydroxides, quaternary amine hydroxides, hydrogen gas with a catalyst such as platinum or palladium and the like; mineral acids such as hydrochloric acid, sulfuric acid and the like, and strong organic acids such as para-toluene sulfonic acid, trifluoracetic acid and the like.

The polyimide-polyamic acids so produced have utility in the preparation of coating compositions for a variety of applications including electronic devices. Depending upon the formulation used, said compositions may or may not be photosensitive.

8) Reaction of Polyimide-polyamic Acid Copolymer with Photosensitive Compound to Form Polyimide-Photosensitive Polyamic Acid Esters The polyimide-polyamic acid copolymers described above may be converted to photosensitive polyimide-polyamic acid esters by chemical conversion of the acid functional groups to photosensitive groups. This conversion may be conducted with alkylating agents such as glycidyl methacrylate, glycidyl acrylate, 2-iodoethyl methacrylate, 2-para-toluenesulfonyl methacrylate and the like to produce photosensitive polyimide-polyamic esters.

9) Preparation of Polyimide-Photosensitive Polyamic Ester Copolymer Using Photosensitive Salt The polyimide-polyamic acid copolymers described above may also be converted to photosensitive polyimide-polyamic acid salts by neutralization of the acid functional groups with an organic bases containing intrinsically photosensitive groups such as N,N-diethylaminoethyl acrylate, N,N-dimethylaminoethyl acrylate, N,N-dimethylaminopropyl acrylate, N,N-diethylaminopropyl acrylate, N,N-diethylaminobutyl acrylate, N,N-dimethylaminobutyl acrylate and similar compounds resulting from the replacement of these acrylates with methacrylates.

To illustrate the present invention, the following examples are provided. These examples, which represent specific embodiments of the present invention, should not be considered as limitation of the invention.

COMPARISON 1

A preheated 500 milliliter, three necked round bottom flask equipped with nitrogen inlet, mechanical stirrer and temperature controller was purged with nitrogen for 30 minutes. The reaction flask was then charged with 4.36 grams (20.00 mmoles) of pyromellitic dianhydride (PMDA), 4.96 grams (40.00 mmoles) of 3-hydroxybenzylalcohol (m-HBA) and 30 mL N-methyl-2-pyrrolidone (NMP). The mixture was heated to 100° C. and stirred at this temperature for three hours. The mixture was then cooled to room temperature and 3.84 grams (20.00 mmoles) of oxydianiline (ODA) were added. The mixture was stirred for a few minutes until the ODA was fully dissolved. 4.00 grams (39.53 mmoles) of triethylamine was then added and the mixture was stirred for 5 minutes. 25.30 grams (66.05 mmoles) of diphenyl(2,3-dihydro-2-thioxo-3-benzoxazoyl)phosphonate (DDTBP) was then added portion-wise within 15 minutes. To this mixture was then added another 250 mL NMP. The reaction mixture was heated to 50° C. and stirred at this temperature for 20 hours. The reaction mixture was then cooled to room temperature and was added slowly to 2500 mL methanol. After stirring for 30 minutes the precipitated product was separated by filtration. The product was then washed with 750 mL methanol. After filtration the product was dried in a vacuum oven at 50° C. for 20 hours. The final product was characterized by $^1$H-NMR, FTIR and inherent viscosity. The inherent viscosity of 1.1 dL/g (0.50 grams in 100 mL of NMP) was indicative of a high degree of polymerization. In the FTIR there was a very small band at 1778 cm$^{-1}$ and $^1$H-NMR showed the presence of the chemical shift of benzyl proton of 3-HBA ester at 5.2 ppm. The integration of benzyl proton peaks versus aromatic peaks revealed that only about 13% imidization occurred in this case and the major part of the product was polyamic acid ester.

COMPARISON 2

A preheated 250 milliliter, three necked round bottom flask equipped with nitrogen inlet, mechanical stirrer and temperature controller was purged with nitrogen for 30 minutes. The reaction flask was then charged with 4.00 grams (12.89 mmoles) of oxydiphthalic anhydride (ODPA), 3.20 grams (25.79 mmoles) of 3-hydroxybenzylalcohol (3-HBA) and 30 mL N-methyl-2-pyrrolidone (NMP). The mixture was heated to 100° C. and stirred at this temperature for three hours. The mixture was then cooled to room temperature and 2.58 grams (12.89 mmoles) of oxydianiline (ODA) were added. The mixture was stirred for a few minutes and ODA was fully dissolved. 4.00 grams (39.53 mmoles) of triethylamine was then added and the mixture was stirred for 5 minutes. 16.30 grams (42.55 mmoles) of diphenyl(2,3-dihydro-2-thioxo-3-benzoxazoyl)phosphonate (DDTBP) was then added portion-wise within 15 minutes. To this mixture was then added another 30 mL NMP. The reaction mixture was heated to 50° C. and stirred at this temperature for 20 hours. The reaction mixture was then cooled to room temperature and was added slowly to 750 mL methanol. After stirring for 30 minutes the precipitated product was separated by filtration. The product was then washed with another 750 mL methanol. After filtration the product was dried in a vacuum oven at 50° C. for 20 hours. The final product was characterized by $^1$H-NMR, FTIR and inherent viscosity. The absence of the peak with the chemical shift of 5.2 in the $^1$H-NMR spectrum corresponding to the chemical shift of benzyl group showed that the ester group was no longer present. The presence of a strong band at 1778 cm$^{-1}$ in the FTIR spectrum characteristic of imides, was evidence of substantial imidization. The inherent viscosity of 1.4 dL/g (0.50 grams in 100 mL of NMP) was indicative of a high degree of polymerization.

COMPARISON 3

A preheated 250 milliliter, three necked round bottom flask equipped with nitrogen inlet, mechanical stirrer and temperature controller was purged with nitrogen for 30 minutes. The reaction flask was then charged with 4.00 grams (12.41 mmoles) of 3,3'4,4'-benzophenonetetracarboxylic dianhydride (BTDA), 3.08 grams (25.79 mmoles) of m-hydroxybenzylalcohol (m-HBA) and 30 mL N-methyl-2-pyrrolidone (NMP).

The mixture was heated to 100° C. and stirred at this temperature for three hours. The mixture was then cooled to room temperature and 2.49 grams (12.41 mmoles) of oxydianiline (ODA) were added. The mixture was stirred for a few minutes until the ODA was fully dissolved. 4.00 grams (39.53 mmoles) of triethylamine was then added and the mixture was stirred for 5 minutes. 15.7 grams (40.56 mmoles) of diphenyl(2,3-dihydro-2-thioxo-3-benzoxazoyl) phosphonate (DDTBP) was then added portion-wise within 15 minutes. To this mixture was then added another 40 mL NMP. The reaction mixture was heated to 50° C. and stirred at this temperature for 20 hours. There was a substantial amount of precipitate in the reaction flask at this stage. The reaction mixture was then cooled to room temperature and was added slowly to 750 mL methanol. After stirring for 30 minutes the precipitated product was separated by filtration. The product was then washed with another 750 mL methanol. After filtration the product was dried in a vacuum oven at 50° C. for 20 hours. The final product was characterized by FTIR. The presence of a strong band at 1778 cm$^{-1}$ in the FTIR spectrum was indicative of substantial imidization. $^1$H-NMR and the inherent viscosity were not measured because of the low solubility of the product in NMP and other common solvents.

COMPARISON 4

A preheated 250 milliliter, three necked round bottom flask equipped with nitrogen inlet, mechanical stirrer and temperature controller was purged with nitrogen for 30 minutes. The reaction flask was then charged with 4.44 grams (10.00 mmoles) of hexafluoroisopropylbis(phthalic dianhydride) (6FDA), 2.50 grams (20.00 mmoles) of 3-hydroxybenzylalcohol (3-HBA) and 30 mL N-methyl-2-pyrrolidone (NMP). The mixture was heated to 100° C. and stirred at this temperature for three hours. The mixture was then cooled to room temperature and 2.00 grams (10.00 mmoles) of oxydianiline (ODA) were added. The mixture was stirred for a few minutes until the ODA was fully dissolved. 4.0 grams (39.53 mmoles) of triethylamine was then added and the mixture was stirred for 5 minutes. 12.65 grams (33.00 mmoles) of diphenyl(2,3-dihydro-2-thioxo-3-benzoxazoyl) phosphonate (DDTBP) was then added portion-wise within 15 minutes. To this mixture was then added another 30 mL NMP. The reaction mixture was heated to 50° C. and stirred at this temperature for 20 hours. The work up was done the same way as comparison 3. The final product was characterized by $^1$H-NMR, FTIR and inherent viscosity. The absence of the peak with the chemical shift of 5.2 in the $^1$H-NMR spectrum corresponding to the chemical shift of benzyl group, showed that the ester group was no longer present. The presence of a strong band at 1778 cm$^{-1}$ in the FTIR spectrum, characteristic of imides was evidence of substantial imidization. The inherent viscosity of this polyimide was 0.19 dL/g (0.50 grams in 100 mL of NMP).

COMPARISON 5

A preheated 125 milliliter, three necked round bottom flask equipped with nitrogen inlet, mechanical stirrer and temperature controller was purged with nitrogen for 30 minutes. The reaction flask was then charged with 2.00 grams (6.45 mmoles) of oxydiphthalic anhydride (ODPA), 0.59 grams (12.81 mmoles) of ethanol and 15 ml N-methyl-2-pyrrolidone (NMP). The mixture was heated to 80° C. and stirred at this temperature for three hours. The mixture was then cooled to room temperature and 1.29 grams (6.45 mmoles) of oxydianiline (ODA) were added. The mixture was stirred for a few minutes until the ODA was fully dissolved. 2.00 grams (19.77 mmoles) of triethylamine was then added and the mixture was stirred for 5 minutes. 8.15 grams (21.28 mmoles) of diphenyl(2,3-dihydro-2-thioxo-3-benzoxazoyl) phosphonate (DDTBP) was then added portion-wise within 15 minutes. To this mixture was then added another 20 mL NMP. The reaction mixture was heated to 50° C. and stirred at this temperature for 20 hours. The reaction mixture was then cooled to room temperature and was added slowly to 400 mL methanol. After stirring for 30 minutes the precipitated product was separated by filtration. The product was then washed with another 500 mL methanol. After filtration the product was dried in a vacuum oven at 50° C. for 20 hours. The final product was characterized by FTIR and inherent viscosity. The presence of a strong band at 1778 cm$^{-1}$ in the FTIR spectrum, characteristic of imide, was indicative of substantial imidization. The inherent viscosity of the product was 0.78 dL/g.

COMPARISON 6

A preheated 125 milliliter, three necked round bottom flask equipped with nitrogen inlet, mechanical stirrer and temperature controller was purged with nitrogen for 30 minutes. The reaction flask was then charged with 2.00 grams (6.45 mmoles) of oxydiphthalic anhydride (ODPA), 0.88 grams (14.64 mmoles) of iso-propanol and 15 mL N-methyl-2-pyrrolidone (NMP). The mixture was heated to 80° C. and stirred at this temperature for three hours. The mixture was then cooled to room temperature and 1.29 grams (6.45 mmoles) of oxydianiline (ODA) were added. The mixture was stirred for a few minutes and ODA was fully dissolved. 2.00 grams (19.77 mmoles) of triethylamine was then added and the mixture was stirred for 5 minutes. 8.15 grams (21.28 mmoles) of diphenyl(2,3-dihydro-2-thioxo-3-benzoxazoyl) phosphonate (DDTBP) was then added portion-wise within 15 minutes. To this mixture was then added another 20 mL NMP. The reaction mixture was heated to 50° C. and stirred at this temperature for 20 hours. The work up was done the same way as comparison 5. After filtration the product was dried in a vacuum oven at 50° C. for 20 hours. The final product was characterized for FTIR and inherent viscosity. The presence of a strong band at 1778 cm$^{-1}$ in the FTIR spectrum, characteristic of imide, was indicative of substantial imidization.

EXAMPLE 1

Step 1: (a). A preheated 250 milliliter, three necked round bottom flask equipped with nitrogen inlet, mechanical stirrer and temperature controller was purged with nitrogen for 30 minutes. The reaction flask was then charged with 2.00 grams (6.44 mmoles) of oxydiphthalic anhydride (ODPA), 0.88 grams (14.66 mmoles) of iso-propyl alcohol and 15 mL N-methyl-2-pyrrolidone (NMP). The mixture was heated to 80° C. and stirred at this temperature for three hours. The mixture was then cooled to room temperature and stored under nitrogen at ambient temperature overnight (solution a).

Step 1: (b). A preheated 250 milliliter, three necked round bottom flask equipped with nitrogen inlet, mechanical stirrer and temperature controller was purged with nitrogen for 30 minutes. The reaction flask was then charged with 1.406 grams (6.44 mmoles) of pyromellitic dianhydride (PMDA), 1.60 grams (12.88 mmoles) of m-hydroxybenzyl alcohol (m-HBA) and 15 mL N-methyl-2-pyrrolidone (NMP). The mixture was heated to 100° C. and stirred at this temperature for three hours. The mixture was then cooled to room temperature and stored under nitrogen at ambient temperature overnight (solution b).

Step 2: Solution (a) added to the solution (b) and 2.58 grams (12.88 mmoles) of oxydianiline (ODA) were added. The mixture was stirred for a few minutes until the ODA was fully dissolved. 4.00 grams (39.53 mmoles) of triethylamine was then added and the mixture was stirred for 5 minutes. 16.30 grams (42.52 mmoles) of diphenyl(2,3-dihydro-2-thioxo-3-benzoxazoyl) phosphonate (DDTBP) was then added portion-wise within 15 minutes. To this mixture was then added another 100 mL NMP. The reaction mixture was heated to 50° C. and stirred at this temperature for 18 hours. The work up was done the same way as comparison 4. The final product was characterized by $^1$H-NMR, FTIR and inherent viscosity. The presence of 1778 cm$^{-1}$ band in the FT-IR spectrum was evidence of imide formation. Analysis of the $^1$H-NMR revealed that ODPA-iPr-ODA was imidized four times more than PMDA-mHBA-ODA. This analysis was based on the comparison of the integration of the chemical shifts of the methyl groups of isopropyl versus the integration of methylene groups of benzyl. The inherent viscosity of the product was 0.84 dL/g.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A process for producing a polyimide-polyamic acid ester copolymer composition comprising reacting at least one diamine, a pyromellitic diacid diester compound; at least one other tetracarboxylic diacid diester compound and phosphoramide in the presence of a base catalyst to form a polyimide-polyamic acid ester copolymer; said phosphoramide is a compound of formula (2):

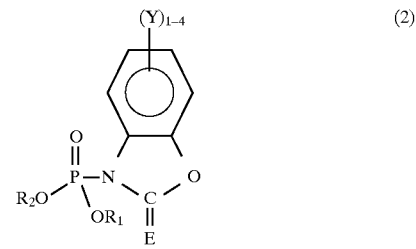

wherein

E is oxygen or sulfur:

$R_1$ and $R_2$ are individually selected from the group consisting of alkyl group having 1–4 carbon atoms; aryl group; substituted aryl group having 1–3 substituents and wherein said substituent are individually selected from halogen group, nitro group, alkyl group having 1–4 carbon atoms and alkoxy group having 1–4 carbon atoms; and each Y is individually selected from hydrogen, halogen group, nitro group, alkyl group having 1–4 carbon atoms and alkoxy group having 1–4 carbon atoms.

2. The process of claim 1, wherein said phosphoramide is diphenyl(2,3-dihydro-2-thioxo-3-benzoxazoyl) phosphonate.

* * * * *